(12) United States Patent
Liu et al.

(10) Patent No.: US 7,041,811 B2
(45) Date of Patent: May 9, 2006

(54) METHOD FOR DETECTING ESCHERICHIA COLI

(75) Inventors: Lu-Yieng Liu, Hsinshu (TW); Te-Yu Chung, Hsinshu (TW); Harn-Jing Terng, Hsinchu (TW)

(73) Assignee: Dr. Chip Biotechnology, Inc., Hsinchu (TW)

( * ) Notice: Subject to any disclaimer, the term of this patent is extended or adjusted under 35 U.S.C. 154(b) by 20 days.

(21) Appl. No.: 10/025,137

(22) Filed: Dec. 19, 2001

(65) Prior Publication Data

US 2003/0113731 A1    Jun. 19, 2003

(51) Int. Cl.
    *C07H 21/04*    (2006.01)
(52) U.S. Cl. .................. 536/23.1; 536/24.3; 536/24.32; 536/24.33
(58) Field of Classification Search .................. 435/6, 435/91.1, 91.2; 536/23.1, 24.3
    See application file for complete search history.

(56) References Cited

U.S. PATENT DOCUMENTS

| | | | |
|---|---|---|---|
| 4,486,539 A | 12/1984 | Ranki et al. | 436/504 |
| 4,816,389 A | 3/1989 | Sansonetti et al. | 435/6 |
| 5,084,565 A | 1/1992 | Parodos et al. | 536/27 |
| 5,354,661 A | 10/1994 | Doyle et al. | 435/7.37 |
| 5,374,718 A * | 12/1994 | Hammond et al. | 536/24.32 |
| 5,693,469 A * | 12/1997 | Hogan | 435/6 |
| 6,060,252 A | 5/2000 | Hellyer et al. | 435/6 |
| 6,207,818 B1 | 3/2001 | Hellyer et al. | 536/24.3 |

FOREIGN PATENT DOCUMENTS

WO    WO 93/03186    2/1993

OTHER PUBLICATIONS

Genbank Accession No. AE005490 (first appeared in Genbank on Jan. 25, 2003).*
Genbank Accession No. AE00346 (Dec. 1, 2000).*
Genbank accession No. Z70523 (Apr. 1996).*
Genbank accession No. D90887 (1997).*
Buck et al; Biotechniques, vol. 27, pp. 528-536, 1999.*
Tijhie et al; J. Microbiol. Meth. vol. 18, pp. 137-150, 1993.*
Accession No. AX002476 (Mar. 2000).*
Accession No. AF175847 (Nov. 2000).*
Genbank accession No. AE015280; Oct. 2002.*
Genbank accession No. AE015281; Oct. 2002.*
Allignment for Genbank Nos. and SEQ ID Nos. 1-8.*
Mansfield et al; The Journal of Infectious Diseases, vol. 184, pp. 803-807, 2001.*
Oswald et al (Infection and Immunity, vol. 68, pp. 64-71; 2000.*

* cited by examiner

Primary Examiner—Jehanne Sitton
(74) Attorney, Agent, or Firm—Fish & Richardson P.C.

(57) ABSTRACT

Specific nucleic acid sequences, e.g., SEQ ID NOs: 1–8, for detecting *Escherichia coli*. Also disclosed is a method of detecting *Escherichia coli*. The method includes providing a sample having a nucleic acid from an unknown microorganism; amplifying the nucleic acid with an upstream primer containing SEQ ID NO: 1 or 3 and a downstream primer containing SEQ ID NO: 2 or 4, each primer being 18–40 nucleotides in length; and detecting an amplification product. Detection of the amplification product, e.g., using SEQ ID NO: 5, 6, 7, or 8 as a probe, indicates the presence of *Escherichia Coli*.

13 Claims, No Drawings

METHOD FOR DETECTING *ESCHERICHIA COLI*

BACKGROUND

Traditional methods of detecting microorganisms rely on time-consuming growth in culture media, followed by isolation and biochemical or serological identification. The entire process usually takes 24–48 hours. Many methods for rapid detection of microorganisms have recently been developed, including miniaturized biochemical analyses, antibody- and DNA-based tests, and modified conventional assays.

Detection of the microorganism *Escherichia coli* in water and food has been considered as an indicator of the possible presence of enteric pathogens. Indeed, certain *E. coli* strains are pathogenic themselves. Rapid and accurate identification of *E. coli* is therefore important for public health.

SUMMARY

The present invention relates to specific nucleic acid sequences for detecting *Escherichia coli*.

In one aspect, this invention features a set of nucleic acids including a first nucleic acid that contains SEQ ID NO: 1 or 3 and a second nucleic acid that contains SEQ ID NO: 2 or 4, each nucleic acid being 18–40 nucleotides in length. These nucleic acids can be used as PCR primers for detecting *E. coli*. In one example, the first nucleic acid contains SEQ ID NO: 1, the second nucleic acid contains SEQ ID NO: 2, and each nucleic acid is 18–40 (e.g., 18–30) nucleotides in length. In another example, the first nucleic acid contains SEQ ID NO: 3, the second nucleic acid contains SEQ ID NO: 4, and each nucleic acid is 24–40 (e.g., 24–32) nucleotides in length.

In another aspect, this invention features a nucleic acid obtained from amplification of an *Escherichia coli* nucleic acid template with an upstream primer containing SEQ ID NO: 1 or 3 and a downstream primer containing SEQ ID NO: 2 or 4, each primer being 18–40 nucleotides in length; the amplification product can be used as a hybridization probe for *E. coli* detection. In one example, the upstream primer contains SEQ ID NO: 1, the downstream primer contains SEQ ID NO: 2, and each primer is 18–40 (e.g., 18–30) nucleotides in length. In another example, the upstream primer contains SEQ ID NO: 3, the downstream primer contains SEQ ID NO: 4, and each primer is 24–40 (e.g., 24–32) nucleotides in length.

In yet another aspect, this invention features a nucleic acid that is 26–1000 (e.g., 26–500, 26–200, or 26–50) nucleotides in length containing SEQ ID NO: 5, 6, 7, or 8, or its complementary sequence. The nucleic acid can simply be SEQ ID NO: 5, SEQ ID NO: 6, SEQ ID NO: 7, or SEQ ID NO: 8, or its complementary sequence. These nucleic acids can be used as hybridization probes for detecting *E. coli*.

Also within the scope of this invention is a method of detecting *Escherichia coli* using two or more of the nucleic acids described above. The method includes (1) providing a sample having a nucleic acid from an unknown microorganism; (2) amplifying the nucleic acid with an upstream primer containing SEQ ID NO: 1 or 3 and a downstream primer containing SEQ ID NO: 2 or 4, each primer being 18–40 nucleotides in length; and (3) detecting an amplification product. Detection of an expected amplification product indicates the presence of *Escherichia coli*. In one example, the detecting step includes hybridizing the amplification product to a nucleic acid probe that is 26–1000 (e.g., 26–500, 26–200, or 26–50) nucleotides in length and contains SEQ ID NO: 5, 6, 7, or 8, or its complementary sequence.

Further within the scope of this invention is a kit for detecting *E. coli*. The kit contains one or more of the nucleic acids described above. It may include other components such as a DNA polymerase, a PCR buffer, or a solid support on which one or more of the above-described probes are immobilized.

The present invention provides a fast, accurate, and sensitive method for *E. coli* detection. The details of one or more embodiments of the invention are set forth in the accompanying description below. Other advantages, features, and objects of the invention will be apparent from the description, and from the claims.

DETAILED DESCRIPTION

The present invention relates to a method for detecting *Escherichia coli*. Specifically, a nucleic acid template from a sample suspected of containing *E. coli* is amplified with a pair of *E. coli*-specific primers. The amplification product, if any, is detected by either gel electrophoresis and staining, or by probe hybridization. Detection of an expected amplification product indicates the presence of *E. coli* in the sample.

The nucleic acid template can be DNA (e.g., a genomic fragment or a restriction fragment) or RNA, in a purified or unpurified form. A nucleic acid template can be obtained from a water sample or a food sample. It can also be obtained from a biological sample (e.g., a specimen from a patient).

The present invention features *E. coli*-specific primers selected from the nucleotide sequence between 81889 and 83238 of *E. coli* genome (GenBank Accession No. AP002562; SEQ ID NO: 12). This region contains three open reading frames (ORFs), i.e., ECs3458, ECs3459 (SEQ ID NO: 13) and ECs3460, encoding three hypothetical proteins with unknown functions. DNA sequence in this region is conserved in both pathogenic and non-pathogenic *E. coli* groups.

In one of the selected primer pairs, the forward primer is a 24 oligo-nucleotide N1 (5'-TGAATGCGCAAGCT-GAAAAAGTAG-3', SEQ ID NO: 3, corresponding to nucleotides 82568–82591 of GenBank Accession No. AP002562), and the reverse primer is another 24 oligo-nucleotide N2 (5'-ACGCCGTTAGGTGTATTGATTGTG-3', SEQ ID NO: 4, corresponding to a complementary sequence of nucleotides 83075–83052 of GenBank Accession No. AP002562).

In another selected primer pair, the forward primer (SEQ ID NO: 1) is the 18 oligo-nucleotide located at the 3'-end of N1, and likewise, the reverse primer (SEQ ID NO: 2) is the 18 oligo-nucleotide located at the 3'-end of N2. A search against GenBank indicates that these two primers are *E. coli*-specific.

In two additional examples, SEQ ID NO: 1 is paired with SEQ ID NO: 4, and SEQ ID NO: 2 is paired with SEQ ID NO: 3 in a PCR reaction.

Typically, a primer is 14–40 nucleotides in length (PCR Application Manual, Boehringer Mannheim, 1995, page 37). In this invention, primers that contain SEQ ID NO: 1, 2, 3, or 4, and have 18–40 (e.g., 18–32) nucleotides in length can be used to amplify an *E. coli* template. *E. coli* sequences can be added to either the 5'-end or the 3'-end of SEQ ID NO: 1, 2, 3, or 4; non-*E. coli* sequences can be added to the 5'-end of SEQ ID NO: 1, 2, 3, or 4. An example of a non-*E.* coli sequence is a sequence containing a restriction site, which can be used to facilitate cloning of the amplification product.

The present invention also features four E. coli-specific probes chosen from the region amplified with primers N1 and N2 described above.

(a) From the sense strand of the amplified nucleic acid sequence:

N1-1: 5'-AATACATAACAGAAACCTGAAACACAA-3' (SEQ ID NO: 5), corresponding to nucleotides 82618–82644 of GenBank Accession No. AP002562; and N1-2: 5'-AAAACACCTCTTCCTGCGATTTCTCAC-3' (SEQ ID NO: 6), corresponding to nucleotides 82758–82784 of GenBank Accession No. AP002562.

(b) From the antisense strand of the amplified nucleic acid sequence:

N2-1: 5'-ATTTTACCTCTTGTCTTCCCGTCTTGG-3' (SEQ ID NO: 7), which is a complementary sequence of nucleotides 82894–82868 of GenBank Accession No. AP002562; and N2-2: 5'-GTTATGTATTGCTGCTGTTTGCGGCG-3' (SEQ ID NO: 8), which is a complementary sequence of nucleotides 82626–82602 of GenBank Accession No. AP002562.

N1-1, N1-2, N2-1, N2-2, and longer probes that contain N1-1, N1-2, N2-1, or N2-2 and have 26–1000 (e.g., 10–500, 10–200, and 10–50) nucleotides in length can each be used for detecting E. coli by hybridizing to an unamplified E. coli nucleic acid or an E. coli nucleic acid amplified with the above-described primer pairs. For instance, the amplification product described above is one of such probes. A search against GanBank indicates that the nucleic acid sequence amplified with primers N1 and N2 is E. coli-specific.

The probes can be immobilized on the surface of a solid support, such as a membrane (a nylon-membrane or a nitrocellulose membrane), a glass, or a plastic polymer. Immobilization of probes to a membrane can be achieved by baking at 80° C. or UV cross-linking. The probes can also be covalently linked to a material (e.g., poly-lysine) coated on the surface of a glass. In addition, a novel method of immobilizing probes on a plastic polymer has recently been developed. See U.S. application Ser. No. 09/906,207. Alternatively, the probes can be synthesized de novo at precise positions on a solid substrate. See Schena et al., 1995, Science 270: 467; Kozal et al., 1996, Nature Medicine 2(7): 753; Cheng et al., 1996, Nucleic Acids Res. 24(2): 380; Lipshutz et al., 1995, BioTechniques 19(3): 442; Pease et al., 1994, Proc. Natl. Acad. Sci. USA 91: 5022; Fodor et al., 1993, Nature 364: 555; and Fodor et al., WO 92/10092.

A target amplification product described above can be detected by binding it to an immobilized probe. To facilitate the detection, a labeled amplification product can be generated with a labeled amplification primer. Alternatively, the labeling can be done, chemically or enzymatically, after amplification. Examples of labeling reagents include, but are not limited to, a fluorescent molecule (e.g., fluorescein and rhodamine), a radioactive isotope (e.g., $^{32}P$ and $^{125}I$), a colorimetric reagent, and a chemiluminescent reagent. Biotin and digoxgenin are frequently used for colorimetric detection on a membrane or a plastic polymer. Fluorescent labels, such as Cy3 and Cy5, are widely used for detection on a glass. In addition, artificial tagging tails (e.g., a protein or its antibody) can be conjugated to the 5'-end of the primers or either end of the probes. See Stetsenko and Gait, 2000, J. Org. Chem. 65(16): 4900.

The specificity of the E. coli detection method of this invention is unexpectedly high. Only E. coli templates can be amplified with the selected primers, and there is no amplification of nucleic acid templates prepared from other bacteria such as Salmonella spp., Shigella spp., Enterobacter aerogenes, Citrobacter freundii, Klebsiella pneumoniae, Staphylococcus aureus, Listeria monocytogenes, Vibrio parahaemolyticus, Bacillus cereus, and Streptococcus aglactiae (see Example 1 below). Most unexpected is the ability of the selected primers to discriminate an E. coli template from a Shigella spp. template, which has not been previously achieved in the art. See, e.g., Hellyer et al., 2001, U.S. Pat. No. 6,207,818. Moreover, amplification of an E. coli template is not affected by the presence of nucleic acid templates prepared from other bacteria (see Example 3 below) or contaminants in a crude sample (see Example 4 below).

The sensitivity of the E. coli detection method of this invention is also unexpectedly high. More specifically, 1 ng and 1 fg of E. coli genomic DNA can be detected on an agarose gel after 20 and 30 cycles of amplification, respectively (see Example 2 below). Hybridization, following PCR amplification, further increases the sensitivity by 5–50 folds (see Example 5 below). Indeed, this method can detect E. coli genomic DNA equivalent to an extract from 1 ml of a 1 cfu/ml culture (see Examples 2 and 5 below).

Also within the scope of this invention is use of E. coli-specific sequences described above in combination with other species-specific nucleic acid sequences for simultaneously identification of multiple microorganisms.

Furthermore, at positions where single nucleotide polymorphisms occur, nucleotide variations are allowed in primers and probes described in this invention. As single nucleotide polymorphisms may be associated with a particular genotype or phenotype, these primers and probes can be used to distinguish and categorize different E. coli strains.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE 1

Amplification and Detection of Escherichia coli using Specific Oligo-Nucleotide Primers (1) Bacteria Strains All bacterial strains used in this example are listed in Table 1 below. Escherichia coli strains used include non-pathogenic and pathogenic subtypes, such as ETEC, EIEC, EPEC, EAggEC and EHEC strains. Non-E. coli bacteria tested include some coliform bacteria and common food-borne pathogen bacteria. These bacterial strains were obtained from different sources, such as Culture Collection and Research Center (CCRC), Hsin-Chu, Taiwan; National Laboratory for Food and Drungs (NLFD), Taipei, Taiwan; American Type Culture Collection (ATCC), Rockville, Md., USA; United States Department of Agriculture (USDA), Washington, D.C., USA; Center of Vaccine Development (CVD), University of Maryland, Baltimore, Md., USA; and Pingtung University of Technology (PT), Pingtung, Taiwan.

One loop of test strains were plated on Luria-Bertani agar (LB; 0.5% yeast extract, 1% trypton, 0.5% NaCl, 1.5–2% agar) and incubated for overnight (14 hr) at 37° C. A single colony was picked and inoculated into 10 ml sterilized LB broth. The culture was incubated for overnight at 37° C. Colony forming unit (cfu) was calculated after serial dilutions, and bacterial genomic DNA was prepared as described below.

(2) Preparation of Bacterial Genomic DNA

Genomic DNA was prepared from 1 ml of bacterial overnight culture. Cells were harvested by centrifugation at 6,000 g for 5 minutes, and were resuspended in 50 ml STET buffer (0.1 M NaCl; 10 mM Tris-HCl, pH 8.0; 1 mM EDTA; 0.05 mg lysozyme; and 5% Triton X-100). Cells were subsequently lysed after incubation for 15 minutes at 37° C. followed by boiling for 10 minutes. DNA-containing supernatant was roughly separated from cell debris after 5 minutes of centrifugation. Genomic DNA was further purified by treatment with phenol/chloroform (1:1), and centrifugation at 10,000g for 10 minutes. The upper layer of the extraction mixture, ca. 40 ml, was transferred into a new eppendorf tube and was ready to be amplified.

(3) Amplification and Detection of Bacterial Genomic DNA with Specific Oligo-Nucleotide Primers Fifty microliters of amplification reaction mixture contains 5 ml 10×Taq DNA polymerase buffer, 5 ml 25 mM MgCl2, 4 ml 2.5 mM dNTPs (Promega, Madison, Wis., USA),

TABLE 1

Bacterial strains

| Number of Strains | Strain | Strain No. and Source |
|---|---|---|
| 8 | Non-pathogenic *E.coli* | FP2-27 (CCRC11509), FP3-27, FP3-28 (ATCC25922), FP3-29 (ATCC11775), FP3-30, FP3-31, FP3-32, FP3-33 |
| 5 | Enteroaggregative *E. coli* (EAggEC) | FP2-32 (TVGH), FP2-33 (CVD), FP2-34 (CVD, O86:H2), FP2-35 (TVGH2), FP2-36 (TVGH) |
| 2 | Enteroinvasive *E. coli* (EIEC) | *E. coli* O124:NM (CCRC15375), *E. coli* O164:H (CVD) |
| 37 | Enterohemoehagic *E. coli* (EHEC) | FP1-37 (CCRC14825), FP1-40 (CCRC15373), FP1-41 (CCRC14824), FP1-42 (CCRC13089), FP3-9 (CCRC14815), FP3-10 (CCRC13084), FP3-11 (CCRC13086), FP3-12 (CCRC35150), FP3-13 (CCRC43890), FP3-14 (CCRC13093), FP3-15 (CCRC13094), FP3-16 (CCRC13095), FP3-17 (CCRC13096), FP3-18 (CCRC13097), FP3-19 (CCRC13098), FP3-20 (CCRC13099), FP2-45 (NLFD I20), FP2-46 (NLFD I61), FP2-47 (NQS317), FP2-48 (USDA014-90), FP2-49 (USDA115-93), FP2-50 (USDA028-00), FP3-1 (USDA 177-93), FP3-2 (USDA042-91), FP3-3 (USDA037-90), FP3-4 (USDA45750), FP3-5 (USDA45753), FP3-6 (USDA45756), FP3-7 (USDA54a-7), FP3-8 (USDAAMF1847), FP3-9 (USDA008-90), FP3-26 (USDA012-89), FP3-21, FP3-22, FP3-23, FP3-24, FP3-25 (USDA008-90) |
| 5 | Enteropathogenic *E. coli* (EPEC) | FP1-35 (CCRC15530), FP1-36 (CCRC15536), FP2-38 (CVD), FP2-39 (CVD), FP240 (NQS) |
| 7 | Enterotoxigenic *E. coli* (ETEC) | FP1-38 (CCRC15372), FP2-25 (CCRC15370), FP2-26 (CCRC15371), FP2-41 (CCRC41443), FP2-42 (WHO103), FP2-43 (WHO110), FP2-44 (WHO112) |
| 56 | Salmonella sp. | FP1-23 (typhi, CCRC14875), FP1-24 (typhimurium, CCRC10747), FP1-25 (salamae, CCRC15450), FP1-26 (typhimurium, CCRC70128), FP1-27 (paratyphi A, CCRC14878), FP1-28 (typhimurium, CCRC12947), FP1-29 (california, CCRC15454), FP1-30 (enteritidis,), FP1-32 (paratyphi B, CCRC14897), FP1-33 (etterbeele, CCRC15455), FP1-34 (postsdam. CCRC15433), FP3-34 (aberdeen, US), FP3-35 (adelaide, US), FP3-36 (albany, USDA), FP3-37 (amager, US), FP3-38 (anatum, PT), FP3-39 (bareilly, USDA), FP3-40 (berta, US), FP3-41 (california, US), FP3-42 (cerro, USDA671D), FP3-43 (cerro, USDA), FP3-44 (chester, USDA), FP3-45 (coleypark, US), FP3-46 (crossness, US), FP3-47 (cubana, USDA), FP3-48 (djakarta, US), FP3-49 (drypool, USDA607E), FP3-50 (dublin, US), FP4-1 (dugbe, US), FP4-2 (enteritidis, ATCC13076), FP4-4 (emek, US), FP4-5 (eppendorf, PT633), FP4-6 (florida, US), FP4-7 (hartford, USDA), FP4-8 (havana, US), FP4-9 (hvttingfoss, USDA), FP4-10 (hvttingfoss, US), FP4-11 (infantis, US), FP4-12 (java, US), FP4-13 (kentuky, US), FP4-14 (litchfield, US), FP4-15 (london, PT1004), FP4-16 (miami, US), FP4-17 (munster, PT1014) FP4-18 (newbrunswick, US), FP4-19 (newington, USDA), FP4-20 (newwington, USDA), FP4-21 (newport, US), FP4-22 (ohio, PT1007), FP4-23 (panama, US), FP4-24 (pomona, USDA), FP4-25 (Poona, USDA), FP4-26 (taksony, USDA1121D), FP4-27 (thomasville, USDA1101E), FP1-31 (typhi, CCRC10746), FP4-3 (enteritidis, US) |
| 1 | *Staphylococcus aureus* | FP1-1 (CCRC10780) |
| 4 | *Shigella* sp. | FP2-18 (dysenteria, CCRC13983), FP2-19 (boydii, CCRC15961), FP2-20 (flexneri, CCRC10772), FP2-21 (sonnei, CCRC10773) |
| 1 | *Streptococcus agalactiae* | FP1-43 (CCRC10787) |
| 1 | *Bacillus cereus* | FP2-16 (CCRC11827) |
| 1 | *Vibrio parahaemolyticus* | FP2-22 (CCRC10806) |
| 1 | *Listeria monocytogenes* | FP2-24 (CCRC14930) |
| 1 | *Enterobacter aerogenes* | FP2-29 (CCRC10370) |
| 1 | *Citrobacter freundii* | FP2-27 (CCRC12291) |
| 1 | *Klebstella pneumoniae* | FP2-30 (CCRC15627) |

1 µl 20 µM of oligo-nucleotide primer N1, 1 µl 20 µM of oligo-nucleotide primer N2, 1 µl DNA template, 0.1 U of Taq DNA polymerase (Promega, Madison, Wis., U.S.A.), and sterilized dH$_2$O.

Amplification was carried out using Peltier-effect Thermal Cyclers (PTC-100, MJ Research Inc., Mass., U.S.A.) as follows: 95° C. for 2 minutes; 30 cycles of 95° C. for 40 sec, 55 ° C. for 40 sec, 72° C. for 40 sec; and a final extension at 72° C. for 6 minutes.

All amplified products (50 µl) were analyzed by electrophoresis on a 2% agarose gel in TAE buffer (40 mM Tris, 20 mM sodiom acetate, 2 mM EDTA, pH adjusted with glacial acetic acid) and stained with ethidium bromide.

The experimental results, summarized in Table 2 below, show that the selected oligo-nucleotide primers are highly specific for detecting *E. coli*. The expected amplified product (molecular weight of 500 bp) could only be detected for all 64 *E. coli* spieces, including 8 non-pathogenic and 56 pathogenic subtypes or serotypes. No amplification product was observed for the other 68 bacterial strains. More specifically, there was no cross reaction between *E. coli* and the 4 *Shigella* spp. strains tested, which is unexpected from previously described PCR-gel-based methods.

EXAMPLE 2

Detection Sensitivity of PCR-gel Analysis (1) Amount of Bacterial Genomic DNA Required for 30 PCR Thermal Cycles Detection sensitivity of the PCR-gel analysis method was determined by titrating the amount of genomic DNA required for amplification. *E. coli* DNA was extracted, purified using QIAamp DNA mini Kit (QIAGEN, Hilden, Germany). Quantification of the purified genomic DNA was performed by electrophretic agarose gel method. DNA marker (Gene Mark, Taiwan, R.O.C.) loaded on the same agarose gel was used as a reference for quantification.

All components except the DNA template in the amplification reaction mixture were the same as described in Example 1, section 3. The amount of genomic DNA tested was in the range of 100 ng to 0.1 fg. Unexpectedly, as low as 1 fg of *E. coli* genomic DNA was detected after amplification using the selected oligo-nucleotide primer pair.

(2) Amount of Bacterial Genomic DNA Required for 20 PCR Thermal Cycles

Less cycle number for amplification reaction means less time needed for *E. coli* detection. Twenty amplification cycles could approximately save 30 minutes than thirty amplification cycles, and the detection sensitivity might be high enough for the purpose of

TABLE 2

*Eseherichia coli* detection using specific oligo-nucleotide primers

| Bacterial strains | Number of strains tested | Number of PCR positive strains | Number of PCR negative strains |
|---|---|---|---|
| *Escherichia coli* | | | |
| Non-pathogenic *E. coli* | 8 | 8 | 0 |
| Enteroaggregative *E. coli* (EAggEC) | 5 | 5 | 0 |
| Enterotoxigenic *E. coli* (ETEC) | 7 | 7 | 0 |
| Enterohemorrhagic *E. coli* (EHEC) | 37 | 37 | 0 |
| Enteropathogenic *E. coli* (EPEC) | 5 | 5 | 0 |
| Enteroinvasive *E. coli* (EIEC) | 2 | 2 | 0 |
| *Shigella* sp. | | | |
| *Shigella dysenteria* | 1 | 0 | 1 |
| *Shigella boydii* | 1 | 0 | 1 |
| *Shigella flexneri* | 1 | 0 | 1 |
| *Shigella sonnei* | 1 | 0 | 1 |
| *Staphylococcus aureus* | 1 | 0 | 1 |
| *Streptococcus agalactea* | 1 | 0 | 1 |
| *Bacillus cereus* | 1 | 0 | 1 |
| *Vibrio parahaemolyticus* | 1 | 0 | 1 |
| *Listeria monocytogenes* | 1 | 0 | 1 |
| *Citrobacter freundii* | 1 | 0 | 1 |
| *Klebsiella pneumoniae* | 1 | 0 | 1 |
| *Enterobacter aerogenes* | 1 | 0 | 1 |
| *Salmonella* sp. | | | |
| *Sal. typhi* | 2 | 0 | 2 |
| *Sal. typhimisum* | 3 | 0 | 3 |
| *Sal. salamae* | 1 | 0 | 1 |
| *Sal. paralyphi* | 2 | 0 | 2 |
| *Sal. california* | 2 | 0 | 2 |
| *Sal. enteritidis* | 3 | 0 | 3 |
| *Sal. etterbeele* | 1 | 0 | 1 |
| *Sal. ostsdam* | 1 | 0 | 1 |
| *Sal. aberdeen* | 1 | 0 | 1 |
| *Sal. albany* | 1 | 0 | 1 |
| *Sal. amager* | 1 | 0 | 1 |
| *Sal. anatum* | 1 | 0 | 1 |
| *Sal. bareilly* | 1 | 0 | 1 |
| *Sal. berta* | 1 | 0 | 1 |

TABLE 2-continued

Escherichia coli detection using specific oligo-nucleotide primers

| Bacterial strains | Number of strains tested | Number of PCR positive strains | Number of PCR negative strains |
|---|---|---|---|
| Sal. cerro | 2 | 0 | 2 |
| Sal. chester | 1 | 0 | 1 |
| Sal. coleypark | 1 | 0 | 1 |
| Sal. crossness | 1 | 0 | 1 |
| Sal. cubana | 1 | 0 | 1 |
| Sal. djakarta | 1 | 0 | 1 |
| Sal. drypool | 1 | 0 | 1 |
| Sal. dublin | 1 | 0 | 1 |
| Sal. dugbe | 1 | 0 | 1 |
| Sal. emek | 1 | 0 | 1 |
| Sal. eppendorf | 1 | 0 | 1 |
| Sal. florida | 1 | 0 | 1 |
| Sal. hartford | 1 | 0 | 1 |
| Sal. havana | 1 | 0 | 1 |
| Sal. hvittingfoss | 2 | 0 | 2 |
| Sal. infantis | 1 | 0 | 1 |
| Sal. java | 1 | 0 | 1 |
| Sal. kentucky | 1 | 0 | 1 |
| Sal. litchfield | 1 | 0 | 1 |
| Sal. london | 1 | 0 | 1 |
| Sal. miami | 1 | 0 | 1 |
| Sal. munster | 1 | 0 | 1 |
| Sal. newbrunswicks | 1 | 0 | 1 |
| Sal. newington | 2 | 0 | 2 |
| Sal. newport | 1 | 0 | 1 |
| Sal. ohio | 1 | 0 | 1 |
| Sal. panama | 1 | 0 | 1 |
| Sal. pomona | 1 | 0 | 1 |
| Sal. poona | 1 | 0 | 1 |
| Sal. thomasville | 1 | 0 | 1 |
| Sal. adelaide | 1 | 0 | 1 |
| Sal. taksony | 1 | 0 | 1 |

*E. coli* detection in food industry. Therefore, we tried to determine the detection limits of genomic DNA and vital cells (cfu, see section 3 below) required for 20 amplification cycles.

Amplification was carried out as described in section 1 of this example, except that 20 amplification cycles were applied instead of 30 cycles. The amount of genomic DNA tested was in the range of 100 ng to 0.1 fg. Unexpectedly, as low as 1 ng of *E. coli* genomic DNA was detected.

(3) Number of Bacterial Cells Required for 20 PCR Thermal Cycles

An overnight culture of pathogenic *E. coil* O157:H7 (H type, CCRC 14825) was grown in LB broth at 37° C., and the cell concentration, colony forming unit/ml (cfu/ml), was determined. Genomic DNA was extracted from 1 ml of a $10^9$ cfu/ml culture, and was serially diluted to concentrations equivalent to extracts from 1 ml of $0-10^7$ cfu/ml cultures.

Amplification was carried out as described in section 2 of this example. Unexpectedly, *E. coli* DNA equivalent to an extract from 1 ml of a 1 cfu/ml culture was detected.

EXAMPLE 3

Detection of *Escherichia coli* in a Bacterial Mixture

Bacterial strains used to make a bacterial mixture include: *Staphylococcus aureus* (CCRC10780), *Salmonella typhimurium* (CCRC10747), *Escherichia coli* (CCRC14825), *Streptococcus agalactea* (CCRC10787), *Bacillus cereus* (CCRC11827), *Shigella dysenteria* (CCRC 13983), *Vibrio parahaemolytticus* (CCRC10806), and *Listeria monocytogenes* (CCRC14930). A single colony was picked from each strain, and was inoculated into 5 ml LB broth for overnight growth at 37° C. with shaking at 100 rpm. Genomic DNA was prepared and amplified as described in Example 1. An expected amplification product (500 bp) was only detected on an agarose gel when *E. coli* was present in the mixture. DNA from other bacterial species did not affect the sensitivity and specificity of the selected amplification primer pair.

EXAMPLE 4

Detection of *Escherichia coli* in a Milk Sample

Whole milk samples were purchased from a local supermarket and were pasteurized. The pathogenic *E. coli* O157: H7 (H type, CCRC 14825) culture was inoculated in a concentration of $10^6$ cfu/ml, and centrifuged at 10,000 g for 5 minutes. Genomic DNA was extracted and serially diluted to the concentrations equivalent to extracts from 1 ml of $0-10^6$ cfu/ml cultures. Amplification was carried out as described in Example 2, section 2.

The expected amplification product (500 bp) was detected on an agarose gel. The sensitivity and specificity of the selected amplification primer pair were not affected by the simple DNA preparation method, or by the presence of other microorganisms and cattle somatic cells in milk.

EXAMPLE 5

Detection of *Escherichia coli* by Hybridization after Amplification (1) Probe Design Four types of oligo-nucleotide probes were designed for hybridization.

Type 1: Four oligo-nucleotides (i.e., N1-1, N1-2, N2-1, and N2-2) were chosen from the region amplified with *E. coli*-specific oligo-nucleotide primers N1 and N2.

Type 2: A DNA probe for positive control of hybridization.

Pco: 5'-$(T)_{25}$-GAGCGGGAAATCGTGCGCGACATCAAGGAG-3' (SEQ ID NO: 9)

Type 3: DNA probes for negative control of hybridization, which can be any non-complementary sequences against the target nucleic acid and have around 25 bases.

Nco1: 5'-$(T)_{25}$-ATGAAGCAYGTCAGGGCRTGGATACCTCG-3' (SEQ ID NO: 10)

Nco2: $dH_2O$

Type 4: An orientation probe, a short oligo-nucleotide with biotin labels at the 5'-end. The sequence is 5'-GTAATACGACTCACTATAGGGC-3' (SEQ ID NO: 11).

(2) Hybridization

Each oligo-nucleotide probe was dissolved in a probe solution (DR. Probsol, DR. Chip Biotechnology Inc., Taiwan) to a final concentration of 10 μM, spotted, and immobilized on a solid substrate (DR. Chip Biotechnology Inc., Taiwan). Amplification was carried out as described in Example 1, except that both primers were labeled with biotin at the 5'-end. The amplification reaction mixture was diluted with a hybridization buffer in a ratio of 1:(50–100). The diluted mixture was boiled for 5 minutes, chilled on ice, and applied to the solid support. Hybridization was performed at 50–55° C. for 1–2 hours in an oven. The solid support was then washed with a wash buffer (0.5 ml) (DR. Wash from DR. Chip Biotechnology Inc., Taiwan) for at least three times. Biotin-specific colorimetric detection was performed by incubating the solid substrate in a Blocking Reagent (Roche) containing alkaline phosphatase-conjugated streptavidin (Promega). The solid substrate was subsequently washed three times with the wash buffer, and incubated with NBT/BCIP solution (Roche) diluted with a detection buffer in a ratio recommended by the supplier for about 10 minutes in dark. Colored type 1 probe spots indicate the presence of an amplification product from *E. coli* genomic DNA. Type 2 probes were stained in all hybridization reactions. No signal was detected from type 3 probes.

(3) Detection Specificity

Genomic DNA isolated from *E. coli*, 8 other bacterial strains, and a mixed bacterial culture containing *E. coli* were amplified and hybridized to the probes. Only samples containing *E. coli* DNA template resulted in colored spots on the solid support. Probe N2-1 showed the highest signal intensity of all type 1 probes under hybridization conditions described above. No signal was detected for the 8 other bacterial samples.

(4) Detection Sensitivity

One-fifth (⅕) volume of the amplification mixture was sufficient for hybridization analysis. *E. coli* DNA templates equivalent to extracts from 1 ml of $10^{0-10^7}$ cfu/ml cultures were amplified and hybridized to the probes. The amount of DNA that could be detected was equivalent to an extract from 1 ml of a 1 cfu/ml culture.

Furthermore, 0.2 ng and 0.02 fg *E. coli* genomic DNA was detected after 20 and 30 cycles of amplification, respectively. Therefore, hybridization analysis is, unexpectedly, 5–50 times more sensitive than analysis on an ethidium bromide-stained agarose gel.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, one can use primers a few nucleotides shorter than SEQ ID NO: 1 or 2 to achieve *E. coli*-specific amplification. Thus, other embodiments are also within the scope of the following claims.

---

What is claimed is:

1. A set of nucleic acid molecules comprising: a first nucleic acid molecule consisting of SEQ ID NO: 1 or SEQ ID NO: 3; and a second nucleic acid molecule consisting of SEQ ID NO: 2 or SEQ ID NO: 4.

2. The set of nucleic acid molecules of claim 1 wherein the first nucleic acid molecule is SEQ ID NO: 1 and the second nucleic acid molecule is SEQ ID NO: 2.

3. The set of nucleic acid molecules of claim 1 wherein the first nucleic acid molecule is SEQ ID NO: 3 and the second nucleic acid molecule is SEQ ID NO: 4.

4. A nucleic acid molecule selected from the group consisting of SEQ ID NO: 5–8 and the complete complements thereto.

5. The nucleic acid molecule of claim 4 wherein the nucleic acid molecule is SEQ ID NO: 5.

6. The nucleic acid molecule of claim 4 wherein the nucleic acid molecule is SEQ ID NO: 6.

7. The nucleic acid molecule of claim 4 wherein the nucleic acid molecule is SEQ ID NO: 7.

8. The nucleic acid molecule of claim 4 wherein the nucleic acid molecule is SEQ ID NO: 8.

9. The set of nucleic acid molecules of claim 1, further comprising a third nucleic acid molecule selected from the group consisting of SEQ ID NOS 5–8 and the complete complements thereto.

10. The set of nucleic acid molecules of claim 9, wherein the third nucleic acid molecule is SEQ ID NO: 5.

11. The set of nucleic acid molecules of claim 9, wherein the third nucleic acid molecule is SEQ ID NO: 6.

12. The set of nucleic acid molecules of claim 9, wherein the third nucleic acid molecule is SEQ ID NO: 7.

13. The set of nucleic acid molecules of claim 9, wherein the third nucleic acid molecule is SEQ ID NO: 8.

* * * * *

SEQUENCE LISTING

```
<160> NUMBER OF SEQ ID NOS: 13

<210> SEQ ID NO 1
<211> LENGTH: 18
<212> TYPE: DNA
<213> ORGANISM: Artificial Sequence
<220> FEATURE:
<223> OTHER INFORMATION: synthetically generated primer

<400> SEQUENCE: 1
cgcaagctga aaaagtag                                                    18

<210> SEQ ID NO 2
<211> LENGTH: 18
<212> TYPE: DNA
```

```
<213> ORGANISM: Artificial Sequence
<220> FEATURE:
<223> OTHER INFORMATION: synthetically generated primer

<400> SEQUENCE: 2
ttaggtgtat tgattgtg                                              18

<210> SEQ ID NO 3
<211> LENGTH: 24
<212> TYPE: DNA
<213> ORGANISM: Artificial Sequence
<220> FEATURE:
<223> OTHER INFORMATION: synthetically generated primer

<400> SEQUENCE: 3
tgaatgcgca agctgaaaaa gtag                                       24

<210> SEQ ID NO 4
<211> LENGTH: 24
<212> TYPE: DNA
<213> ORGANISM: Artificial Sequence
<220> FEATURE:
<223> OTHER INFORMATION: synthetically generated primer

<400> SEQUENCE: 4
acgccgttag gtgtattgat tgtg                                       24

<210> SEQ ID NO 5
<211> LENGTH: 27
<212> TYPE: DNA
<213> ORGANISM: Artificial Sequence
<220> FEATURE:
<223> OTHER INFORMATION: synthetically generated probe

<400> SEQUENCE: 5
aatacataac agaaacctga aacacaa                                    27

<210> SEQ ID NO 6
<211> LENGTH: 27
<212> TYPE: DNA
<213> ORGANISM: Artificial Sequence
<220> FEATURE:
<223> OTHER INFORMATION: synthetically generated probe

<400> SEQUENCE: 6
aaaacacctc ttcctgcgat ttctcac                                    27

<210> SEQ ID NO 7
<211> LENGTH: 27
<212> TYPE: DNA
<213> ORGANISM: Artificial Sequence
<220> FEATURE:
<223> OTHER INFORMATION: synthetically generated probe

<400> SEQUENCE: 7
attttacctc ttgtcttccc gtcttgg                                    27

<210> SEQ ID NO 8
<211> LENGTH: 26
<212> TYPE: DNA
<213> ORGANISM: Artificial Sequence
<220> FEATURE:
<223> OTHER INFORMATION: synthetically generated probe

<400> SEQUENCE: 8
gttatgtatt gctgctgttt gcggcg                                     26
```

<210> SEQ ID NO 9
<211> LENGTH: 55
<212> TYPE: DNA
<213> ORGANISM: Artificial Sequence
<220> FEATURE:
<223> OTHER INFORMATION: synthetically generated probe

<400> SEQUENCE: 9
tttttttttt tttttttttt tttttgagcg ggaaatcgtg cgcgacatca aggag        55

<210> SEQ ID NO 10
<211> LENGTH: 54
<212> TYPE: DNA
<213> ORGANISM: Artificial Sequence
<220> FEATURE:
<223> OTHER INFORMATION: synthetically generated probe

<400> SEQUENCE: 10
tttttttttt tttttttttt tttttatgaa gcaygtcagg gcrtggatac ctcg         54

<210> SEQ ID NO 11
<211> LENGTH: 22
<212> TYPE: DNA
<213> ORGANISM: Artificial Sequence
<220> FEATURE:
<223> OTHER INFORMATION: synthetically generated probe

<400> SEQUENCE: 11
gtaatacgac tcactatagg gc                                            22

<210> SEQ ID NO 12
<211> LENGTH: 1350
<212> TYPE: DNA
<213> ORGANISM: Escherichia coli

<400> SEQUENCE: 12
atgacgcgca tgaaatatct ggtggcagcc gccacactaa gcctgttttt ggcgggttgc     60
tcggggtcaa aggaagaagt acctgataat ccgccaaatg aaatttacgc gactgcacaa    120
caaaagctgc aggacggtaa ctggagacag gcaataacgc aactggaagc gttagataat    180
cgctatccgt ttggtccgta ttcgcagcag gtgcagctgg atctcatcta cgcctactat    240
aaaaacgccg atttgccgtt agcgcaggct gccatcgatc gttttattcg ccttaacccg    300
acccatccga atatcgatta tgtcatgtac atgcgtggcc tgaccaatat ggcgctggat    360
gacagtgcgc tgcaagggtt ctttggcgtt gaccgtagcg atcgcgatcc tcaacatgca    420
cgagctgcgt ttagtgactt ttccaaactg gtgcgcggct atccaaacag tcagtacacc    480
accgatgcca ccaaacgtct ggtattcctg aaagatcgtc tggcgaaata tgaatactcc    540
gtggccgagt actatacaga acgtggcgca tgggttgccg tcgttaaccg cgtagaaggc    600
atgttgcgcg actacccgga tacccaggct acgcgtgatg cgctgccgct gatggaaaat    660
gcataccgtc agatgcagat gaatgcgcaa gctgaaaaag tagcgaaaat catcgccgca    720
aacagcagca atacataaca gaaacctgaa acacaaaacg gcagcccttg agctgccgtt    780
tttttattct gtcagttgtg aaactgaagc gatttagtca ctatcgatct catcaaatat    840
ggctcgcttt gagatattcc tcaagtaaaa aaacacctct tcctgcgatt tctcacaaaa    900
aagattcgtt gacaaaaagt gacaaaatta tgagatttcc atcacacatt ttgacatcag    960
gaacggtatg ctgaattcac caagacggga agacaagagg taaaatttat gacaatgaac   1020

-continued

| | |
|---|---|
| attaccagca aacaaatgga aattactccg gccatccgcc aacatgtcgc agaccgtctc | 1080 |
| gccaaactgg aaaaatggca aacacatctg attaatccac atatcattct gtccaaagag | 1140 |
| ccacaagggt ttgttgctga cgccacaatc aatacaccta acggcgttct ggttgccagt | 1200 |
| ggtaaacatg aagatatgta caccgcaatt aacgaattga tcaacaagct ggaacggcag | 1260 |
| ctcaataaac tgcagcacaa aggcgaagca cgtcgtgccg caacatcggt gaaagacgcc | 1320 |
| aacttcgtcg aagaagttga agaagagtag | 1350 |

<210> SEQ ID NO 13
<211> LENGTH: 207
<212> TYPE: DNA
<213> ORGANISM: Escherichia coli

<400> SEQUENCE: 13

| | |
|---|---|
| ttgagctgcc gttttttttat tctgtcagtt gtgaaactga agcgatttag tcactatcga | 60 |
| tctcatcaaa tatggctcgc tttgagatat tcctcaagta aaaaaacacc tcttcctgcg | 120 |
| atttctcaca aaaagattc gttgacaaaa agtgacaaaa ttatgagatt tccatcacac | 180 |
| attttgacat caggaacggt atgctga | 207 |